US010548771B2

(12) United States Patent
Coleman et al.

(10) Patent No.: US 10,548,771 B2
(45) Date of Patent: Feb. 4, 2020

(54) DEVICE AND PROCEDURE TO TREAT PRESBYOPIA

(71) Applicants: Carl Zeiss Meditec AG, Jena (DE); Jackson Colemann, Haworth, NJ (US)

(72) Inventors: Jackson Coleman, Haworth, NJ (US); Dan Z. Reinstein, London (GB); Manfred Dick, Gefell (DE)

(73) Assignee: CARL ZEISS MEDITEC AG, Jena (DE)

( * ) Notice: Subject to any disclaimer, the term of this patent is extended or adjusted under 35 U.S.C. 154(b) by 516 days.

(21) Appl. No.: 14/016,337

(22) Filed: Sep. 3, 2013

(65) Prior Publication Data
US 2014/0066909 A1   Mar. 6, 2014

Related U.S. Application Data

(60) Provisional application No. 61/697,384, filed on Sep. 6, 2012.

(51) Int. Cl.
*A61F 9/008* (2006.01)

(52) U.S. Cl.
CPC .................... *A61F 9/008* (2013.01)

(58) Field of Classification Search
CPC ....... A61F 9/008–2009/00897; A61F 9/00827; A61F 9/00838; A61F 9/007–9/013
USPC .............................................. 606/4–6, 10–12
See application file for complete search history.

(56) References Cited

U.S. PATENT DOCUMENTS

| | | | |
|---|---|---|---|
| 5,984,916 A | 11/1999 | Lau | |
| 6,491,688 B1* | 12/2002 | Lin | A61F 9/008 606/4 |
| 6,726,679 B1 | 4/2004 | Dick et al. | |
| 7,252,662 B2* | 8/2007 | McArdle | A61F 9/008 128/898 |
| 7,351,241 B2 | 4/2008 | Bendett et al. | |
| 2002/0055736 A1* | 5/2002 | Horn | A61F 9/013 606/26 |
| 2004/0199149 A1* | 10/2004 | Myers | A61F 9/008 606/4 |
| 2006/0095023 A1* | 5/2006 | Loesel | A61F 9/008 606/5 |

(Continued)

OTHER PUBLICATIONS

Coleman DJ. Unified model for accommodative mechanism. AM J Ophthalmol. Jun. 1970;69 (6):1063-79.

(Continued)

*Primary Examiner* — Gary Jackson
*Assistant Examiner* — Jonathan Kuo
(74) *Attorney, Agent, or Firm* — Leydig, Voit & Mayer, Ltd.

(57) ABSTRACT

A treatment apparatus for surgical correction of presbyopia or defective eyesight in an eye of a patient. The treatment apparatus includes a laser device configured to treat lens tissue of the eye by irradiation of pulsed laser radiation with the laser radiation being focused on target points arranged in a pattern within the lens. An interface supplies measurement data on parameters of the eye and/or defective-eyesight data on the eyesight defect to be corrected in the eye, and defines a volume located within the lens using the supplied measurement data and defective-eyesight data, the volume being defined so as to achieve the desired correction of presbyopia or defective eyesight when removed.

10 Claims, 3 Drawing Sheets

(56) References Cited

U.S. PATENT DOCUMENTS

| | | | |
|---|---|---|---|
| 2007/0185475 A1* | 8/2007 | Frey | A61F 9/008 606/4 |
| 2007/0203478 A1* | 8/2007 | Herekar | A61F 9/008 606/10 |
| 2008/0275433 A1 | 11/2008 | Russman et al. | |
| 2010/0312231 A1* | 12/2010 | Singh | A61F 9/008 606/5 |

OTHER PUBLICATIONS

Coleman DJ. On the hydraulic suspension theory of accommodation. Trans Am Ophthamol Soc. Dec. 1986;84:846-68.
Coleman DJ, Fish SK. Presbyopia, accommodation, and the mature catenary. Ophthalmology. Sep. 2001;108(9):1544-51.

* cited by examiner

DEVICE AND PROCEDURE TO TREAT PRESBYOPIA

FIELD

The invention is related to a device and a procedure which enables treatment of presbyopia in human eyes.

BACKGROUND

Cataract surgery of the human eye lens is the most commonly performed operation world-wide, with about 20 million procedures performed a year. Cataract numbers increase more and more with aging society. Because of age as well as other factors such as UV radiation, the human lens becomes increasingly opaque until the patient becomes blind. Well-established cataract surgery, which is mostly done by phacoemulsification of the natural lens within the capsular bag and implantation of a new artificial intraocular lens, can avoid blindness and give patients clear vision again.

Before the onset of cataract, on-going growth and hardening of the natural human lens over time can reduce the ability of the lens to accommodate or change shape in order to see both distant and near objects. By the age of 40, the accommodation range can become less than 3 D, which strongly influences near vision in emmetropic eyes. This is called presbyopia. Reading glasses are helpful to overcome the effects of presbyopia, but don't address the root cause. Other approaches like multifocal intraocular lenses, multifocal corneal laser ablation profiles in LASIK (laser in situ keratomileusis) procedures, intracorneal inlays, Femtosecond (or other) laser incisions inside the corneal stroma like INTRACOR® or photothermal keratoplasty can regain near vision. These surgical treatment options are based on using multifocality to extend the depth of focus, but at a cost of contrast sensitivity or also requiring a monovision or micromonovision.

Accommodating artificial intraocular lenses like AT-45 CrystaLens, Human Optics 1CU and others have been developed as a potential solution to recreate the accommodative response artificially, however, studies have shown that there is negligible forward movement of the lens and so any increase in near vision with these lenses comes from a small depth of field increase due to the asphericity in the lenses. Certainly, accommodative lenses have been unable to give the patient the 3 D of accommodative range that is required.

Lens capsule refill technologies are under development to bring a gel into the capsular bag after phacoemulsification of the natural lens. However, these lens capsule refill technologies cannot currently adjust the refractive power or the dimensions of this gel IOL accurately enough during the refilling process. There are also serious problems with posterior lens capsule opacification.

Over the last 10 years, femtosecond (or other) laser surgery of the human cornea has been introduced into clinical practice. Femtosecond (or other) laser technology uses the phenomenon of photodisruption to create microbubbles within the cornea to separate tissue. By scanning the laser spot, 3-dimensional cuts can be performed to create a flap as part of a LASIK procedure (U.S. Pat. No. 5,984,916) or also to cut out a precise intra-stromal lenticule, which can then be extracted through a small incision to correct the manifest refraction with the VisuMax femtosecond (or other) laser system (US 2008/0275433).

Femtosecond (or other) laser cataract surgery has also been successfully introduced in recent years. In this procedure, a femtosecond (or other) laser is used to open the anterior capsular bag by creating a centered, round, custom-designed anterior capsulotomy. Using a femtosecond (or other) laser has advantages over manual capsulotomy as the cut is more accurate. The femtosecond (or other) laser is then used to break up the cataract lens by making a crossed cut or by chopping the lens into tiny parts which can then be easily removed from the capsular bag (U.S. Pat. No. 7,351,241).

Femtosecond (or other) laser surgery for the treatment of presbyopia has also been proposed in the past. The main approach was to soften the natural human lens with theory that the lens would regain elasticity and accommodative amplitude. The lens softening can be done by cutting gliding planes or producing microbubbles in order to produce a more elastic sponge-like structure. (See: EP 1212022 B 1). This approach is mainly based on the Helmholtz model of accommodation where the stiffness of the lens material plays the most important role.

SUMMARY

In an embodiment, the present invention provides a treatment apparatus for surgical correction of presbyopia or defective eyesight in an eye of a patient. The treatment apparatus includes a laser device configured to treat lens tissue of the eye by irradiation of pulsed laser radiation with the laser radiation being focused on target points arranged in a pattern within the lens. An interface supplies measurement data on parameters of the eye and/or defective-eyesight data on the eyesight defect to be corrected in the eye, and defines a volume located within the lens using the supplied measurement data and/or defective-eyesight data, the volume being defined so as to achieve the desired correction of presbyopia or defective eyesight when removed.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

An aspect of the present invention is to provide a method, a device and arrangement to treat presbyopia of the human eye lens using a minimally invasive procedure using femtosecond (or other) laser technologies. Thereby the basis of the proposed treatment may be the Coleman catenary theory of accommodation and presbyopia, as described in:

Coleman, D J, *Unified model for accommodative mechanism.* Am. J. Ophthalmol, 1970, 69(6): 1063-79;

Coleman, D J, *On the hydraulic suspension theory of accommodation*, Trans Am. Ophthalmol Soc., 1986, 84: 846-68;

Coleman D J, Fish S K, *Presbyopia, accommodation, and the mature catenary*, Ophthalmology, 2001, 108(9): 1544-51.

This theory of accommodation holds that the lens shape change is caused by vitreous support pushing the lens forward into a conoid or catenary-like shape supported by the anterior zonules, rather than capsular force rounding up the natural lens. This theory claims that the loss of accommodation is caused by an increase in the volume of the lens with age, such that the vitreous support of the lens can no longer produce a steep anterior radius of curvature due to the ocular anterior segment dimension restrictions. Reduction of peripheral lens volume would re-establish the catenary potential of a steep central optical curvature and restore the natural accommodative mechanism.

The aim of the minimally invasive femtosecond (or other) laser treatment is to shrink the peripheral circle of the lens outside the optical zone to reduce the lens volume, so that hydraulic lens movement can take place and contribute in an improved manner to an increased accommodative amplitude of the eye.

Figure 1A:
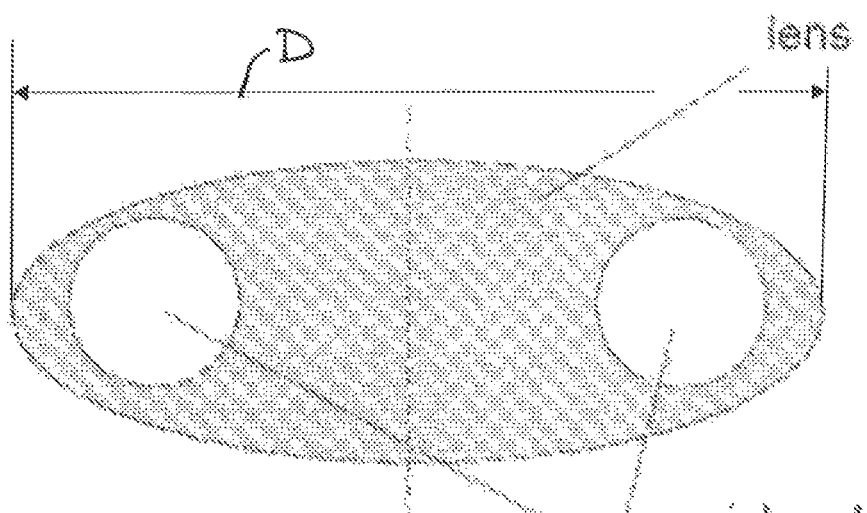
FIG. 1A shows a peripheral laser treatment zone outside an optical zone of the lens.
Figure 1B:
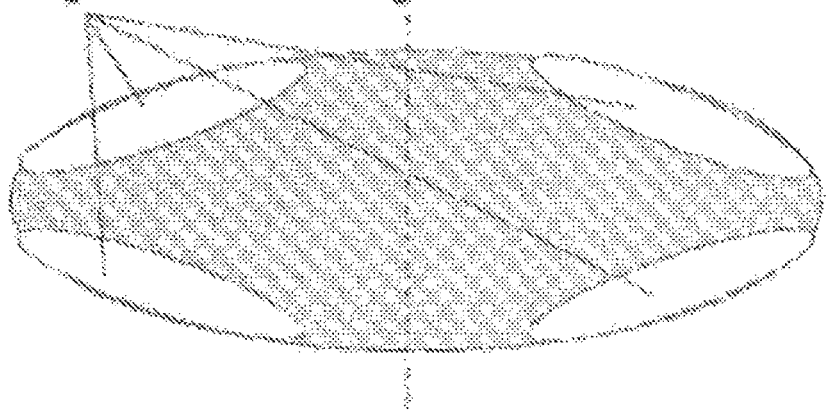
FIG. 1B shows an outside lens shape change after shrinking of the lens due to laser treatment of FIG. 1A.

Thereby the lens shrinkage treatment is foreseen to be minimally invasive, so that no cataract will be induced. It has been shown in animal and human studies, that femtosecond (or other) laser induced photodisruption can be applied without inducing cataract changes in the crystalline lens. Therefore a femtosecond (or other) laser can be used to place photodisruption bubbles in the periphery of the lens. This treatment will lead to gas production, but also a reduction of tissue because of the photodisruption process. The treatment can be applied symmetrically as shown in FIG. 1, but also asymmetric treatment options are possible, that e.g. only a shrinking in the anterior part of the lens will occur. To reduce immediate over-production of gas bubbles and to ensure that this gas will be absorbed by the fluid of the eye and transported away, a special treatment protocol over time and space is proposed in embodiments of the invention.

Figures 2A, 2B:
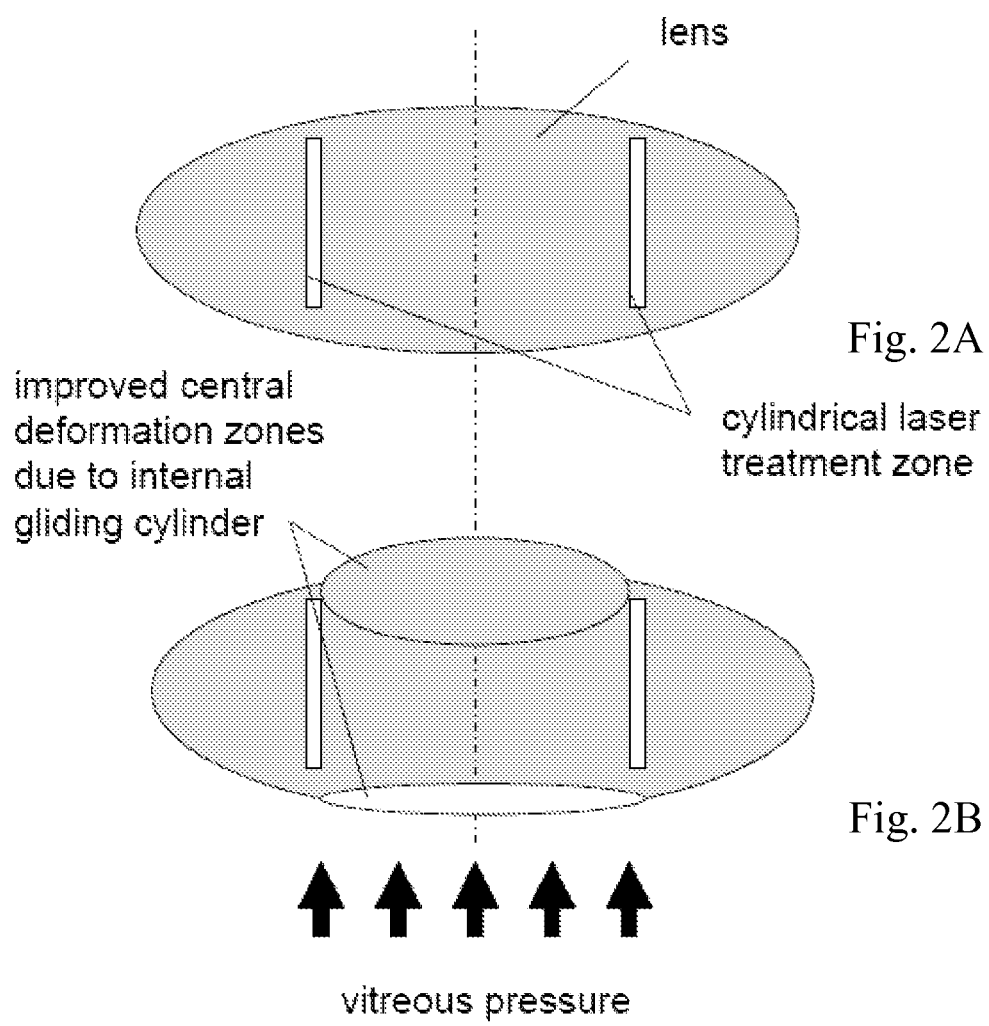
FIG. 2A shows a cylindrical laser treatment zone outside an optical zone of the lens.
FIG. 2B shows an internal gliding cylinder, due to tissue softening, that results in improved central forward movement of lens tissue because of vitreous pressure, which causes improved accommodation in presbyopic lenses due to the treatment of FIG. 2A.
Figures 3A, 3B:
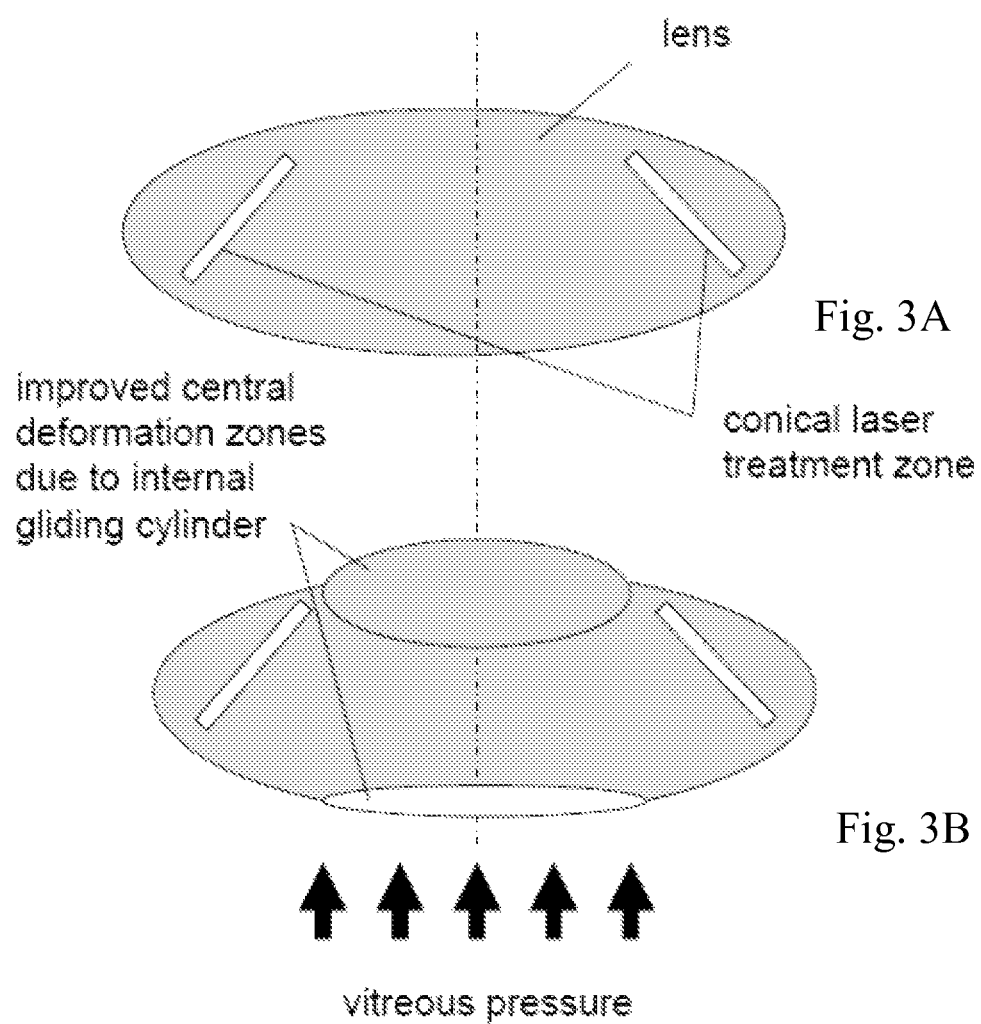
FIG. 3A shows a conical laser treatment zone outside of the optical zone of the lens.
FIG. 3B shows an internal gliding cylinder, due to tissue softening, that results in improved central forward movement of lens tissue because of vitreous pressure, which causes improved accommodation in presbyopic lenses due to the treatment of FIG. 3A

This protocol includes several treatment sessions where spots at different spacing, in a navigated manner, will be applied into the circular periphery outside the optical zone of the lens. One example is to treat 3 times over the course of 4 weeks (i.e. 2 and 4 weeks after the first treatment) and use a spot separation of 10 times the spot diameter of minimal 5 µm and maximal 50 µm. Thereby the spot positioning will be shifted from one treatment session to the other with help of registration and recommended OCT (optical coherence tomography) navigation in between the earlier applied spot patterns in a well-defined manner as shown in FIG. 2.

The aim of the minimally invasive femtosecond (or other) laser treatment is to shrink the peripheral circle diameter D of the lens outside the optical zone to reduce the lens volume, so that hydraulic lens movement can take place and contribute in an improved manner to an increased accommodative amplitude of the eye.

As the laser induced shrinking of the peripheral lens volume will also lead to a change of the static refractive power of the lens, in a further extension of the invention an aberrometer is used to obtain a refractive or wavefront measurement during and/or after the laser treatment. With the help of this accurate measurement of refractive power, changes not only with regard to sphere and cylindrical values as well as higher order aberrations like spherical aberrations and coma will be possible, it also will become possible to tune the refractive power of the lens and the eye within some dioptre and sub-dioptre range to stay at emmetropia or also to become an emmetropic eye, if there is myopia or hyperopia. So this new method is also suited to treat static refractive errors within an eye. As the shrinking will lead to a desired shrinking in the anterior periphery of the lens, the radius of curvature of the anterior surface of the lens will become smaller and the refractive power higher. So one approach is to change the laser treatment zone (see FIG. 1) from a symmetrical ring with circular cross section into non circular cross section shapes which will induce a flatter shape of the posterior lens surface due to the shrinking, which can be e.g. a triangle shape with one corner at the outside of the laser treatment ring zone.

In order to place the laser treatment spots into planned positions within the lens tissue, the device may include a navigation, for example based on optical coherence tomography, confocal laser scanning or Scheimpflug imaging. As a further advantage, this imaging modality can also be used to track the geometrical shape changes of the lens geometry which will correspond to the change in refractive power measured with help of aberrometry.

A dynamic OCT imaging after laser treatment during the accommodation of the eye will be very helpful to understand the effect of laser shrinking of the lens with regard to increase of accommodative power. Instead of a dynamic OCT imaging a dynamic high speed ultrasound imaging is also helpful in order to see the peripheral lens regions behind the iris during accommodation of the individual eye. This information can be used to plan the next treatment session to be individualized and optimized with regard to the unique geometries of each patient's eye.

In a further version of the invention not only photodisruption with nonthermal interaction with lens tissue by help of especially fs-laser pulses is used, but also longer pulse lengths from ps-, ns-, µs- and ms-range are intended, which have more thermal side effects but also a photodisruptive potential to create gas bubbles. These thermal side effects lead to thermally induced tissue shrinking in combination with the photodisruptive tissue elimination.

A further version of the invention is the use of cw (continuous wave)-laserradiation which only heats up the lens tissue without a generation of bubbles. So the heating will lead to a coagulation of the lens tissue with the effect of tissue shrinking. The application time will be in the ms-s-time range in this treatment version.

As it is known that thermally induced cataract can occur, the treatment parameter with all longer pulse as well as cw-laser treatment methods which use thermal coagulation to shrink the lens tissue have to be carefully adjusted.

So the wavelengths of the lasers used will be within the transmission range of the anterior chamber of the human eye (near UV, visible and near infrared region: 350-1300 nm). The laser powers which will be applied will be less than 1 W.

In an embodiment, the invention relates to a planning tool to calculate the laser treatment for the methods described above. This planning tool generates control data for such procedures based on input of measurement data of the eye and/or of the refractive error to be corrected, and defines a volume located within the lens which would achieve the desired refractive correction if removed.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for surgical correction of presbyopia in an eye of a patient, the method comprising:
    defining a lens volume reduction based on measurement data of the eye, wherein the lens volume reduction defines an amount of shrinkage of a peripheral circle diameter of the lens of the eye sufficient to achieve the desired correction of presbyopia; and
    treating the lens using at least one laser device by irradiating the eye with femtosecond pulses of laser radiation and longer pulses of laser radiation directed at laser treatment spots, wherein the femtosecond pulses of laser radiation are configured to cause photodisruption in the peripheral lens tissue of the eye, wherein the longer pulses of laser radiation are configured to cause thermally induced tissue shrinkage in the peripheral lens tissue of the eye, and wherein the longer pulses of laser radiation have pulse lengths from the picosecond to millisecond range,
    wherein the laser treatment spots are placed at planned positions within peripheral lens tissue;
    wherein the planned positions within the peripheral lens tissue are selected so as to bring about the lens volume reduction by the photodisruption and by the thermally induced tissue shrinkage,
    wherein the planned positions within the peripheral lens tissue include planned positions for laser treatment spots of a first treatment session and planned positions for laser treatment spots of at least one subsequent treatment session, and
    wherein the planned positions for laser treatment spots of the at least one subsequent treatment session are determined based on an imaging of the eye performed after the first treatment session.

2. The method of claim 1, wherein the first treatment session is intended to bring about less than the total lens volume reduction.

3. The method of claim 1, wherein the planned positions for laser treatment spots of the at least one subsequent treatment session are shifted from registered positions of laser treatment spots of the first treatment session.

4. The method according to claim 3, wherein the planned positions for the laser treatment spots of the at least one subsequent treatment session are shifted from the registered positions of the laser treatment spots of the first treatment session based on a navigation.

5. The method according to claim 4, wherein the navigation is based on an imaging of the eye using at least one of optical coherence tomography (OCT), confocal laser scanning, Scheimpflug imaging, and ultrasound imaging.

6. The method according to claim 1, wherein the planned positions for laser treatment spots of the at least one subsequent treatment session are determined based on changes of the lens geometry resulting from the first treatment session.

7. The method according to claim 1, wherein the first treatment session and the at least one subsequent treatment session collectively bring about the lens volume reduction.

8. The method according to claim 1, wherein the planned positions for laser treatment spots of the at least one subsequent treatment session are located in between the planned positions for the laser treatment spots of the first treatment session.

9. The method according to claim 1, wherein the planned positions for the laser treatment spots of the first treatment session and/or the at least one subsequent treatment session are placed in the periphery of the lens such that photodisruptive bubbles can be transported away without causing problems in the treatment zone.

10. A method for surgical correction of presbyopia in an eye of a patient, the method comprising:
    generating control data for placing, by a treatment apparatus, laser treatment spots into planned positions within peripheral lens tissue of the eye;
    defining a lens volume reduction using measurement data on parameters of the eye for surgical correction of presbyopia, wherein the lens volume reduction defines an amount of shrinkage of a peripheral circle diameter of a lens of the eye sufficient to achieve a desired correction of presbyopia; and
    treating the lens using at least one laser device by irradiating the eye with femtosecond pulses of laser radiation and longer pulses of laser radiation directed at the laser treatment spots, wherein the femtosecond pulses of laser radiation are configured to cause photodisruption in the peripheral lens tissue of the eye, wherein the longer pulses of laser radiation are configured to cause thermally induced tissue shrinkage in the peripheral lens tissue of the eye, and wherein the longer pulses of laser radiation have pulse lengths from the picosecond to millisecond range,
    wherein the planned positions within the peripheral lens tissue are selected so as to bring about the lens volume reduction through the photodisruption and the thermally induced tissue shrinkage,
    wherein the planned positions within the peripheral lens tissue include planned positions for laser treatment spots of a first treatment session and planned positions for laser treatment spots of at least one subsequent treatment session, and wherein the planned positions for laser treatment spots of the at least one subsequent treatment session are determined based on an imaging of the eye performed after the first treatment session.

* * * * *